United States Patent [19]
Nash et al.

[11] Patent Number: 5,662,681
[45] Date of Patent: Sep. 2, 1997

[54] SELF LOCKING CLOSURE FOR SEALING PERCUTANEOUS PUNCTURES

[75] Inventors: John E. Nash, Downington; Herbert G. Kephart, Glen Mills, both of Pa.

[73] Assignee: Kensey Nash Corporation, Exton, Pa.

[21] Appl. No.: 635,166

[22] Filed: Apr. 23, 1996

[51] Int. Cl.$^6$ .................................................. A61B 17/08
[52] U.S. Cl. ............................................. 606/213; 604/285
[58] Field of Search ................................. 606/213, 215, 606/216, 232, 151; 623/11; 600/32; 604/51, 168, 900, 285

[56] References Cited

U.S. PATENT DOCUMENTS

| | | |
|---|---|---|
| 5,282,827 | 2/1994 | Kensey et al. |
| 5,312,435 | 5/1994 | Nash et al. |
| 5,411,520 | 5/1995 | Nash et al. |

*Primary Examiner*—Michael Buiz
*Assistant Examiner*—Tina T. D. Pham
*Attorney, Agent, or Firm*—Caesar, Rivise, Bernstein, Cohen & Pokotilow, Ltd.

[57] ABSTRACT

A closure device for sealing a percutaneous puncture in the wall of a blood vessel, duct, or lumen of a living being. The puncture has opening in the wall of the blood vessel, duct, or lumen, and a tract contiguous therewith. The closure device is arranged to be inserted into the puncture by an introducing instrument and basically comprises an anchor, a collagen plug, a flexible filament, and locking disk. The anchor is arranged to be brought into engagement with the interior tissue of the vessel, duct, or lumen contiguous with the opening, while the plug and the locking disk are located within the tract. The filament is arranged to be pulled to apply tension thereto. While tension is applied to the filament the locking disk and the plug are moved in the tract toward the anchor. The filament comprises an engagement loop, a first extending portion, and a second extending portion. The engagement loop is coupled to the locking disk. The first extending portion of the filament extends through the plug between the anchor and the locking disk. The second extending portion of the filament extends through the plug from the anchor to the locking disk and through the engagement loop. The second extending portion of the filament is arranged to be pulled in a proximal direction to apply tension to the filament and to cause the engagement loop to frictionally engage the second extending filament portion to hold the locking disk with respect to the anchor and with the plug interposed therebetween.

26 Claims, 3 Drawing Sheets

5,662,681

SELF LOCKING CLOSURE FOR SEALING PERCUTANEOUS PUNCTURES

SPECIFICATION

This invention relates generally to medical devices and more particularly to hemostatic closures for sealing percutaneous incisions or punctures in blood vessels or other body vessels, ducts, or lumens.

In U.S. Pat. No. 5,282,827, entitled Hemostatic Puncture Closure System and Method of Use, which is assigned to the same assignee as this invention, and whose disclosure is incorporated by reference herein, there are disclosed variant systems for sealing a percutaneous incision or puncture in a blood vessel. Those systems basically comprise a closure, an introducer, and a deployment instrument including a carrier for the closure. The closure has three basic components, namely, a sealing member, an intraarterial anchor member, and a positioning member. The sealing member is in the form of an elongated rod-like plug, e.g., a compressed hemostatic, resorbable collagen sponge or foam. This plug member is arranged for sealing the puncture. The anchor member is an elongated, stiff, low-profile member which is arranged to be seated inside the artery against the artery wall contiguous with the puncture. The anchor member is molded of non-hemostatic resorbable polymer similar to resorbable suture. The positioning member comprises a filament, e.g., a resorbable suture. The filament connects the anchor member and the collagen plug (sealing member) in a pulley-like arrangement, and includes a portion extending outside the patient's body. The outwardly located filament portion is arranged to be pulled, i.e., tension applied thereto, after the anchor member is located within the interior of the artery and in engagement with the inner wall of the artery contiguous with the incision or puncture. The pulling on the filament causes its pulley arrangement to move the plug in the puncture tract toward the anchor member. A tamping member, forming a portion of the deployment instrument, is slid down the filament while it is maintained in tension to gently tamp the plug in the puncture tract to cause the plug to deform so that its diameter increases somewhat. Tension is maintained on the filament by use of an externally located spring during the tamping procedure. The expansion of the plug within the tract is enhanced by the fact that it is formed of a compressed collagen so that it expands in the presence of blood within the puncture tract. The expansion of the plug within the puncture tract serves to hold it in place. Moreover, the closure quickly becomes locked in place through the clotting of the hemostatic collagen plug within the puncture tract. The spring serves to hold the plug in its deformed state until such time that the plug is locked in place by the hemostatic clotting action. Once this has occurred, so that the plug is effectively locked within the puncture tract, the externally located spring can be removed. This typically occurs after approximately 30 minutes. After the spring is removed, the filament is severed at the top of the tamping member. The tamping member is then removed and the remaining portion of the filament is cut subcutaneously prior to the discharge of the patient. The portion of the filament connecting the anchoring member to the plug remains in tension, thereby holding the closure permanently in place until it is eventually absorbed by the patient's body.

In U.S. Pat. No. 5,411,520, which is assigned to the same assignee as this invention, and whose disclosure is also incorporated by reference herein, there is disclosed a system for sealing a percutaneous incision or puncture in a blood vessel or other lumen. That system includes a closure, similar in most respects to the closures disclosed in the above mentioned patent out also having means for preventing the sealing portion of the closure from gaining access into the interior of the artery. In particular, the closure of that application includes a spacer member interposed between the anchor member and the plug member to keep the plug member in the puncture tract, but spaced from the opening in the artery.

In U.S. Pat. No. 5,312,435, which is also assigned to the same assignee as this invention, and whose disclosure is also incorporated by reference herein, there is disclosed another closure for sealing a percutaneous puncture in a blood vessel. That closure is similar in construction to the closures of the above mentioned patents except that its anchoring means comprises a generally elongated member formed of a resorbable material having reinforcing means, e.g., a filament, ribbon or mesh also formed of a resorbable material, extending along substantially the length thereof and fixedly secured thereto, e.g., molded in situ therein. The reinforcing means prevents the anchoring member from breaking apart and separating from the closure in the event of a failure in the closure or an incorrect deployment.

While the closures of the aforementioned patents are suitable for their intended purposes, they still may leave something to be desired from the standpoint of ensuring, via simple means, that there is no movement between the sealing member and the anchor member while the closure is being locked in place through the clotting of the hemostatic collagen plug within the puncture tract.

OBJECTS OF THE INVENTION

Accordingly, it is a general object of this invention to provide a closure device and methods of use for sealing a percutaneous puncture in a vessel, duct, or lumen, and which addresses that need.

It is a further object of this invention to provide a vessel puncture closure device including an anchoring portion located within the vessel and filament means connected to the anchoring means, wherein the closure is arranged to be locked in place in response to the application of tension to the filament means.

It is a further object of this invention to provide a vessel puncture closure device including an anchoring portion located within the vessel and an sealing portion located within the puncture tract, and filament means extending therebetween, with the closure being arranged to be locked in place in response to the application of tension to the filament means.

It is a further object of this invention to provide a vessel puncture closure device including an anchoring portion located within the vessel, a sealing portion located within the puncture tract, filament means extending therebetween, and locking means, with the locking means of the closure being arranged so that the sealing portion and anchoring portion are held in position relative to each other but the application of tension on the filament means.

It is still a further object of this invention to provide vessel puncture closure device which is simple in construction, easy to use, safe, effective, and reliable.

SUMMARY OF THE INVENTION

These and other objects of this invention are achieved by providing a closure device for sealing a percutaneous puncture in the wall of a vessel (e.g., blood vessel), duct, or lumen of a living being. The puncture comprises an opening in the wall of the vessel, and a tract contiguous with the opening and extending through tissue overlying the vessel.

The closure device basically comprises anchoring means, sealing means, filament means, and locking means. The anchoring means is arranged to be brought into engagement with the interior tissue of the vessel contiguous with the opening. The sealing means and the locking means are arranged to be located within the tract. The filament means is coupled to the anchoring means, the sealing means, and the locking means. The sealing means is arranged to be moved toward the anchoring means to a puncture sealing position in the tract.

The filament means comprises an engagement portion, a first filament portion, and a second filament portion. The engagement portion of the filament means is coupled to the locking means. The first filament portion of the filament means extends between the anchoring means and the locking means. The second filament portion of the filament means extends from the anchoring means through the tract and is arranged to be pulled in a proximal direction to cause the engagement portion of the filament means to engage the second filament portion to hold the locking means in position, whereupon the sealing means is held in the puncture sealing position.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED EMBODIMENT

Figure 4:
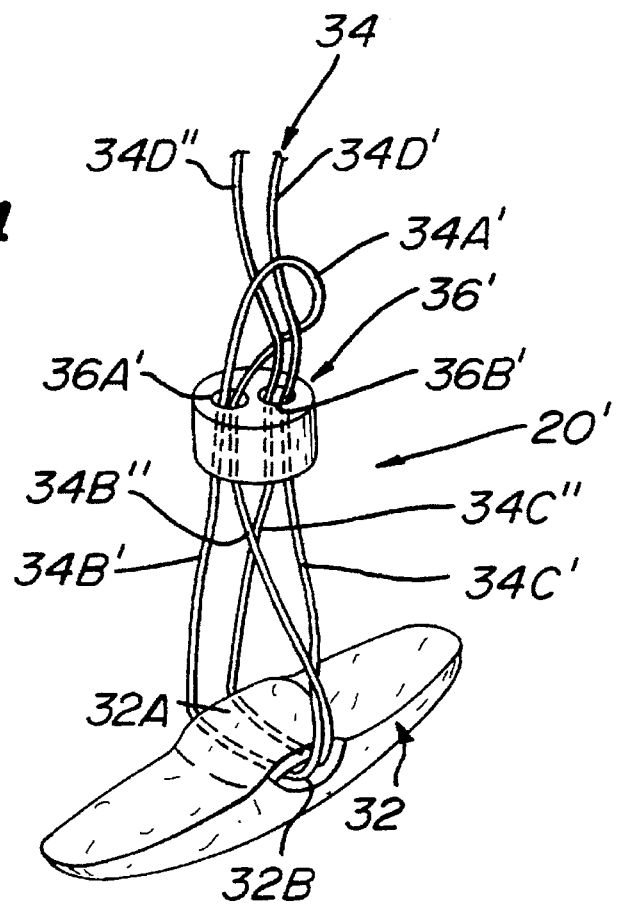
FIG. 4 is an exploded isometric view of a portion of an alternative closure of this invention.

Referring now in greater detail to the various figures of the drawings wherein like reference characters refer to like parts, here is shown at 20 a closure device constructed in accordance with one embodiment of this invention and disposed within the distal end of a deployment instrument 100. In FIG. 4 there is shown an alternative closure 20' which is constructed in accordance with this invention and which, like closure 20, is arranged to be located in the distal end of the deployment instrument 100.

Both of the closure devices 20 and 20' are arranged for sealing a percutaneous puncture in any vessel, duct, or lumen in the body of a living being after having been introduced therein by the deployment instrument 100. For the remainder of this application, the closures 20 and 20' will be described with reference to sealing a percutaneous puncture in a blood vessel, e.g., the femoral artery.

Figure 3:
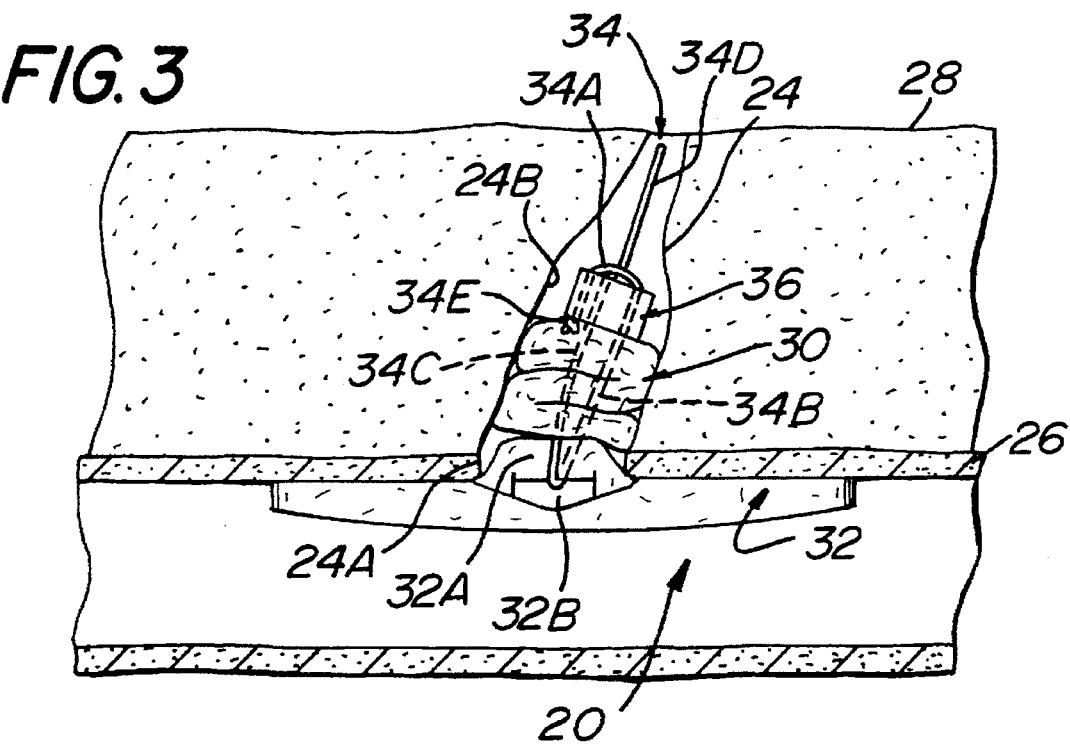
FIG. 3 is a partial sectional view showing the closure of FIG. 1 in its fully deployed state sealing a percutaneous puncture or incision in a blood vessel of a living being.

In FIG. 3 the closure 20 is shown in its fully deployed state sealing a percutaneous puncture 24 in the femoral artery 26. As can be seen therein the percutaneous puncture 24 includes an opening or hole 24A in the artery 26 wall and a tract 24B leading up to the opening 24A. By tract it is meant the passageway in the tissue located between the artery 26 and the skin 28 of the being, and which is formed when the artery is punctured percutaneously.

To expedite the understanding of the construction and operation of this invention, the closure 20' will be described first. To that end, the closure 20 has four basic components, namely, a sealing member or plug 30, an intraarterial anchor member 32, a positioning filament 34, and a locking member 36. The anchor member 32 and the filament 34 are each constructed in accordance with the teachings of the aforementioned '827 patent (i.e., U.S. Pat. No. 5,282,827). The plug 30 is also constructed in accordance with the teachings of the '827 patent, except for apertures (to be described later) in that member and the manner that the filament member is coupled to it.

Like the closures of the '827 patent, the closures of this invention are arranged to be deployed into the percutaneous puncture via the same basic introducing instrument as described in that patent. That instrument is designated by the reference number 100, and only the distal portion of it is shown herein in the interest of drawing simplicity. Thus, the deployment instrument 100 basically comprises a tubular carrier 102 formed of a somewhat flexible material to enable the carrier tube to freely pass through any conventional introducer sheath (not shown) into an operative position within the patient's artery. The distal end of the carrier tube includes a rigid sleeve or bypass tube 104 to enable the carrier tube to be inserted through the hemostasis valve (not shown) of the introducer sheath, through the sheath, and out the distal end thereof into the artery. The proximal end of the deployment instrument 100 includes a filament tensioning assembly (not shown). An elongated tamping member 106 is located within the carrier tube. The tamper member 106 is constructed in accordance with the teachings of the '827 patent and includes a central passageway 108 extending longitudinally therethrough.

The closure 20 is arranged to disposed within the distal end of the tubular carrier 102 to ready it for deployment into the puncture in a similar manner to that described in the '827 patent. In particular, the anchor member 32 is disposed longitudinally within the bypass tube 104 laterally of the central longitudinal axis of the carrier tube 102. The plug 30 is located within the carrier tube just behind (proximally) of the anchor member 32 and on the opposite side of the central longitudinal axis. The locking member 36 is located proximally of the plug 30, while the tamping member is located proximally of the locking member in the carrier tube.

The filament member 34 is identical in construction to that of the aforementioned '827 patent, except for the path through which it extends. In particular, and as will be described in detail later, the filament member is an elongated flexible resorbable member, e.g., a suture, of a single strand or multiple strands, and which is defined by plural sequentially located portions or sections. As can be seen clearly in FIG. 2 starting from one free end of the filament, it includes a loop portion 34A located immediately adjacent the locking member on the proximal side of the locking member, a first extending section 34B extending from the locking member 36 to the anchor member 32, where the first extending filament section passes through a passageway in the anchor member, a second extending filament section 34C extending from the passageway in the anchor member to the plug 30, where the second extending filament section passes through apertures in the plug 30, and a third extending filament section 34D extending from the apertures in the plug, through the loop portion 34A of the filament on the proximal side of the locking member 36 through the passageway 108 in the tamper 106 from whence it terminates in another free end (not shown).

The sealing member or plug 30 basically comprises a strip of a compressible, resorbable, collagen foam, which is arranged to be straightened and compressed transversely to its longitudinal axis when it is loaded in the carrier tube 102 of the deployment instrument 100. Prior to loading into the deployment instrument, the closure 20 looks somewhat like that shown in FIG. 2. Thus, as can be seen, the plug 30 includes three apertures, 30A, 30B, and 30C through which portions of the filament 34 extend (as will be described later). When the plug is compressed and linearized for location within the distal end of the carrier tube of the deployment instrument the apertures 30A–30C are oriented to extend substantially transversely to the longitudinal axis of the plug and parallel to one another. The compression of the plug may result in the apertures 30A–30C being embedded within the body of the collagen making up the plug, like shown in FIG. 1.

The aperture 30C is located close to the proximal end of the plug, the aperture 30A is located close to the distal end of the plug, and the aperture 30B is located approximately midway between the apertures 30A and 30B. The apertures 30A–30C serve as passageways through which the first and second extending sections 34B and 34C, respectively, of the filament 34 pass to couple the anchor member 32 to the locking member 36, with the plug interposed therebetween.

Figure 1:
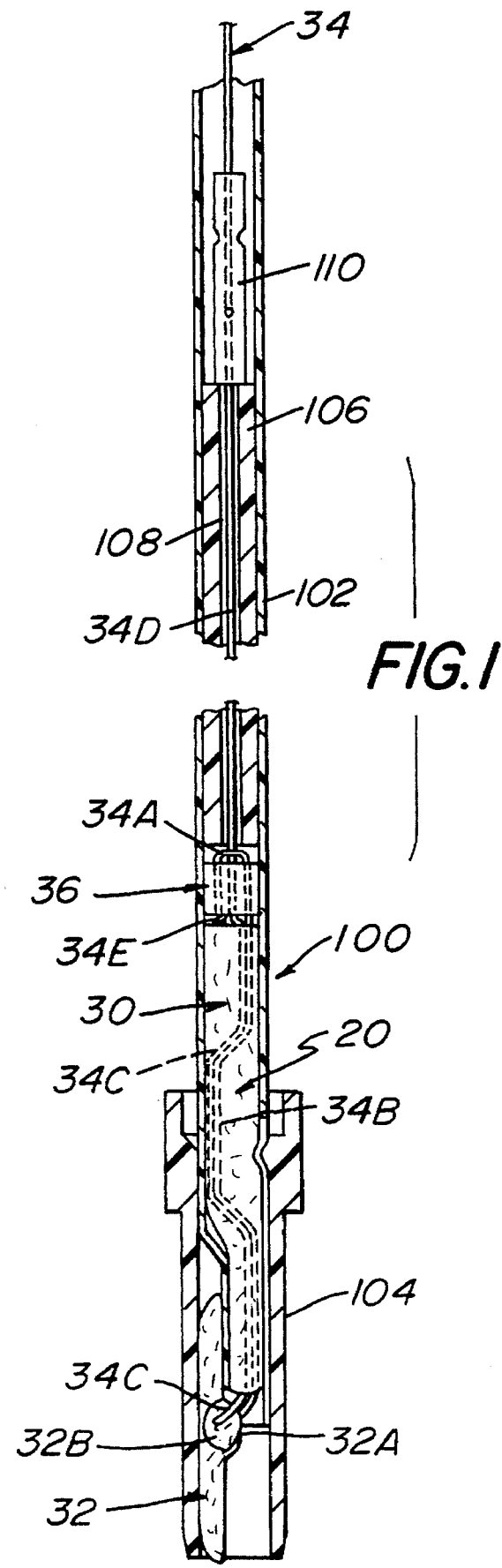
FIG. 1 is a longitudinal sectional view of the distal end of an introducing instrument holding one embodiment of the closure of this invention prior to its deployment to seal a percutaneous incision or puncture in a blood vessel, duct, or lumen of a living being.
Figure 2:
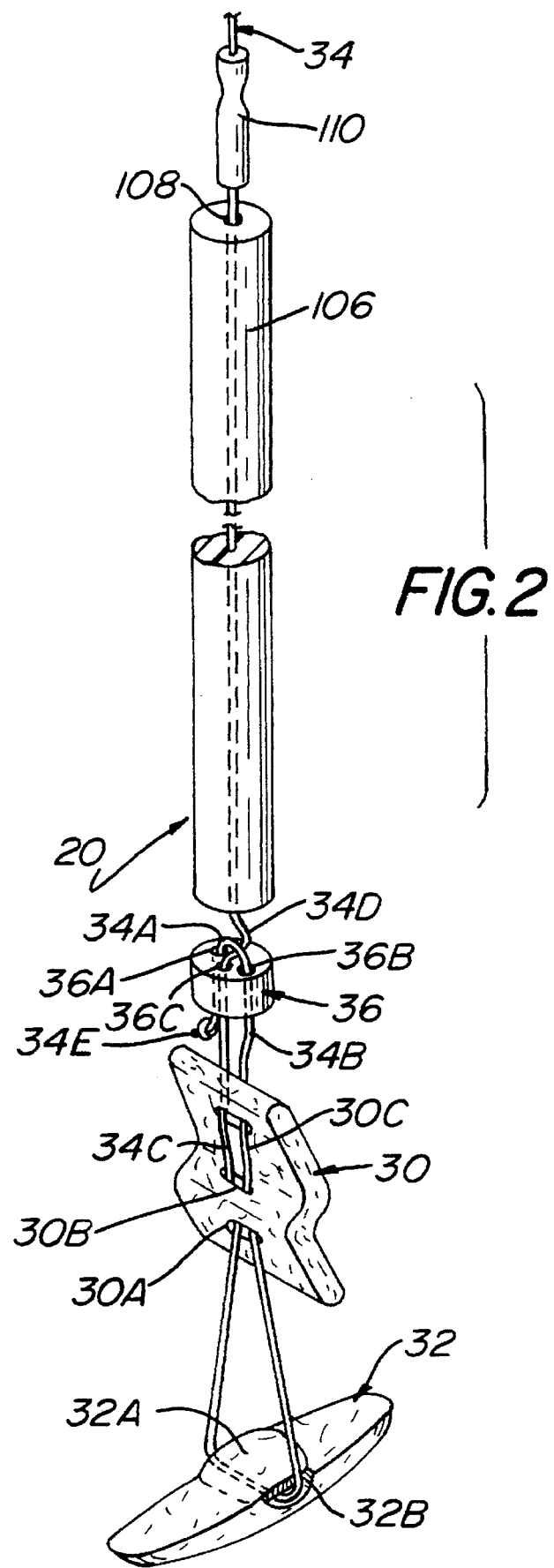
FIG. 2 is an enlarged exploded isometric view of the closure of FIG. 1, shown after assembly of the components thereof, but prior to disposition within the introducing instrument of FIG. 1.

The locking member 36 basically comprises a disk or washer-like member, preferably formed of a resorbable material, such as that forming the anchor member. The locking member has a at least two apertures extending therethrough from its proximal side to its distal side, through which portions of the filament 34 extend. In the embodiment of FIGS. 1, 2 and 4, the locking member 36 includes three apertures, namely, 36A, 36B, and 36C, whereas the locking member of the closure 20' (to be described later) only has two apertures.

The anchor member 32 is similar to the anchor member of the '827 patent. Thus, it basically comprises a thin, narrow, strip or bar of material which is sufficiently rigid such that once it is in position within the artery, it is resistant to deformation to preclude it from bending to pass back through the puncture through which it was first introduced. The anchor member 32 has a generally planar top surface having a hemispherical dome-like projection 32A located at the center of the top surface. The top of the projection is slightly flat. As can be seen in FIG. 3, the dome-like projection 32A is arranged to extend into the opening 24A in the artery wall 26 when the anchor member 32 is properly deployed within that artery, i.e., when the top surface of the anchor member is in engagement with the interior of the artery contiguous with the opening 24A.

A passageway 32B of generally trapezoidal cross section, but with slightly rounded corners, extends transversely across the anchor member 32 below the projection 32A and close to the bottom surface of the anchor member. A portion of the filament 34 at the interface of the first and second sections 34B and 34C, respectively, is arranged to be threaded through this passageway to couple the anchor member 32 and locking member 36 together in a pulley-like arrangement with the plug 30 interposed between the locking member and the anchor member.

The pulley-like arrangement of the filament cooperates with the tamping member 106 to effect the movement and deformation of the plug 30 within the tract 24B once the anchor member 32 is in its desired position in the artery (i.e., against the inner surface of the artery wall). This action occurs by applying tension to the filament during the tamping operation, as will be described later. As will also be described in detail later, the tensioning of the filament also has the effect of causing the loop section 34A of the filament 34 to frictionally engage the second extending section 34D of the filament to lock the closure in place, thereby sealing the puncture.

Referring again to FIG. 2, it can be seen that when the closure is assembled the one free end of the filament 34 contiguous with the loop section 34A extends through the aperture 36A in the locking member 36 and is formed into a knot 34E. The knot is located immediately adjacent the distal side of the locking member and is arranged to engage that side contiguous with the aperture 36A when tension is applied to the filament. The next contiguous section of the filament 34 constitutes the heretofore identified loop section 34A. The loop portion extends between the aperture 36A and the aperture 36B on the proximal side of the locking member. The next contiguous section of the filament 34 constitutes the heretofore identified first extending section 34B. That section extends between the aperture 36B and one side of the passageway 32B in the anchor member 32. In particular, the first extending section 34B extends in one direction through the proximally located aperture 30C in the plug, in the opposite direction through the intermediate aperture 30B in the plug, and in the one direction through the distally located aperture 30A in the plug. From there the first extending section 34B of the filament 34 extends into one side of the passageway 32B of the anchor member 32. The next contiguous section of the filament 34 constitutes the theretofore identified second extending section 34C. That section extends between the other side of the passageway 32B in the anchor member 32 and the locking member 36. In particular, the second extending section 34C of the filament extends back through the apertures 30A, 30B, and 30C of the plug in the same path as the first section 34B. The second extending filament section 34C then passes through the aperture 36C in the locking member 36 from the a distal side to the proximal side thereof. The next contiguous section of the filament 34 constitutes the heretofore identified third extending filament section 34D. That section extends from the proximal side of aperture 36C under the loop section 34A of the filament through the central passageway 108 in the tamper member 106 from the distal side to the proximal side thereof. When the closure 20 is located within the deployment instrument the proximal end portion of the filament, i.e., section 34D, extends through the tensioning assembly (not shown) and out of the deployment instrument. A holding sleeve or tag 110, e.g., a stainless steel tube; like that of the '827 patent, is crimped onto the filament section 34D so that it engages the proximal end of the tamping member 106 to hold that member in place.

Deployment of the closure 20 by the deployment instrument 100 is as follows. The deployment instrument is inserted into introducer sheath (which had been previously positioned in the same manner as described in the '827 patent), so that the bypass tube 104 of the carrier tube 102 passes through the hemostasis valve (not shown) of the introducer sheath (not shown). The deployment instrument is then pushed fully down the introducer sheath, whereupon the bypass tube remains in the sheath and the anchor member 32 is deposited in the artery 26 beyond the distal end of the introducer sheath. The deployment instrument is then operated to determine if the anchor member 32 has been properly deployed. To that end, the introducer sheath is held by the user to prevent axial movement and the instrument is carefully withdrawn from it. This action causes the anchor member 32 to engage or catch on to the distal end of the introducer sheath. As the anchor member catches on the distal end of the introducer, resistance will be felt by the user to indicate appropriate deployment of the anchor as described in the '827 patent.

Once the anchor member 32 has been properly deployed, the plug 30 is deployed into the puncture tract. To that end the introducer sheath and the deployment instrument are held together and withdrawn as a unit from the puncture, whilst swinging the unit toward a vertical orientation. This action causes the anchor 32 to engage or catch onto the inner surface of the artery 26 wall contiguous with the opening 24A. The introducer sheath and the instrument are then pulled further outward. Inasmuch as the anchor member is trapped against the interior of the artery wall, the continued retraction of the introducer sheath and deployment instrument causes the filament 34 to pull the plug 30 out of the carrier tube 102 of the deployment instrument and into the puncture tract 24B. As the introducer and deployment instrument come out of the puncture tract, continuous steady resistance will be felt as the tensioner assembly of the deployment instrument controls the force on the filament 34 during the retraction procedure.

Continued retraction of the introducer and the instrument brings the tamping member out of the free end of the instrument.

The retraction of the introducer sheath and the deployment instrument carries the plug 30 into engagement with the exterior of the artery wall immediately adjacent the opening 24A. In fact, continued retraction causes the filament to somewhat deform the plug, i.e., cause it to deform radially outward. The existence of blood within the puncture tract further contributes to the deformation of the plug 30, since its collagen foam expands in the presence of blood. The retraction procedure continues to pull the introducer and instrument up the filament until the tag 110 is exposed. At this point the plug 30 will be located in the puncture tract contiguous with the opening in the artery, and the locking member located immediately proximally of the plug.

The plug is now ready to be tamped By the tamping member 106. To achieve that end, the user quickly compacts the collagen of the plug by gently tensioning the filament by pulling on the introducer sheath and instrument in the proximal direction with one hand. The tamping member is then manually slid down the filament section 34D by the user's other hand so that it enters the puncture tract 24B and engages the proximal side of the locking member to cause it to compress the plug. A few gentle compactions are adequate to achieve the desired result, i.e., to assist the plug 30 to conform to the artery contiguous with the opening 24A and to assist to lock said the plug in place until hemostasis occurs (which happens very quickly, thereby locking the closure in place).

It should be noted that during the tamping action care must be taken to maintain tension on the filament section 34D at a load greater than that used on the tamping member 106 to ensure that the tamping action doesn't propel the plug 30 into the interior of the artery.

The application of tension to filament section 34D causes any slack in the filament between the knotted end 34E and the portion of the third section 34D passing between the loop section 34A and the adjacent proximal side of the locking member, to be taken up. This action also causes the loop section 34A to close about and tightly frictionally engage the filament section 34D extending between it and the proximal side of the locking member 36. The frictional engagement between the tightened loop portion 34A and the third extending filament section 34D ensures that that filament cannot slip. Thus, the two sections of the filament extending between the locking member 36 and the anchor member, i.e., the first extending section 34B and the second extending section 34C, are held in tension. This action automatically holds the closure in place so that the locking member cannot move away from the anchoring member. Since the plug 30 is compressed between the anchoring member and the locking member, it is retained or locked in position within the puncture tract and cannot move away from the anchoring member, even before the blood clots in the plug.

Thus, with the subject invention, once the filament is pulled tight to cause its loop portion to lock on its third extending section, the portion of the filament extending between the tamping member and the tag can be severed and the tamping member and the deployment instrument removed from the puncture tract. This action leaves the closure locked in place within the puncture. The locking of the closure 20 in place is also aided by virtue of the clotting of the hemostatic collagen plug. In this regard within a few hours after deployment, the anchor member 32 will be coated with fibrin and thus attached firmly to the arterial wall, thereby eliminating the possibility of distal embolization. After approximately thirty days, only a small deposit of anchor material will remain. In fact, resorption of all components will have occurred after approximately sixty days. Moreover, since the plug 30 is formed of compressed collagen or other hydrophilic material it also expands automatically in the presence of blood within the puncture tract 24A when deployed, thereby further contributing to the plug's enlargement.

As should be appreciated from the forgoing, the deployment of the closure device 20 of this invention is accomplished in the same general manner as described in the '827 patent, except that no external spring is necessary to maintain tension on the filament until hemostasis occurs to lock the plug within the puncture tract. Instead, the tensioning of the filament during the closure placement procedure automatically locks the closure in place, even though hemostasis may not have occurred yet.

In order to ensure that no portion of the anchor member can break off and separate from the closure 20 when the anchor member 32 is deployed within the blood vessel, the anchor member includes a flexible strip (not shown) e.g., a resorbable suture, serving as reinforcing means in accordance with the teachings of the aforementioned U.S. Pat. No. 5,312,435.

In FIG. 4 there is shown a portion of the alternative closure 20' of this invention. The closure 20' includes the same basic components as the closure 20, except that the locking member include only two apertures, and the filament is doubled over itself and threaded through the anchor member, the plug, and the locking member in a different arrangement than the closure 20. In the interest of brevity the common components of the closure 20' will be given the same reference numbers and their construction and operation will not be reiterated. Moreover, the plug 30 is not shown in FIG. 4 in the interest of drawing simplicity.

As can be seen in FIG. 4, the locking member of the closure 20' is designated by the reference number 36' and includes only two apertures 36A' and 36B'. The filament 34' of the closure 20' is of the same basic construction as the filament 34, but is doubled over itself and is extended through the anchor member 32, the plug 30, and the locking member 36' in a somewhat different manner. In this regard, the loop section 34A' of the filament 34 is disposed on the proximal side of the locking member 36' with the contiguous sections 34B' and 34B" of the loop 34A' extending through the plug's aperture 36A'. The sections 34B' and 34B" also extend through the apertures in the plug 30 (not shown in FIG. 4) in the same manner as described earlier and into the passageway 32A of the anchor member 32 from opposite directions. The next contiguous sections of the doubled over filament 34' are designated by the reference numbers 34C' and 34C" and extend back from opposite sides of the passageway 32A through the apertures in the plug 30, also in the same manner as described earlier. The sections 34C' and 34C" then pass into the aperture 36B' in the locking member from the distal side thereof. The next contiguous sections of the doubled over filament 34' are designated by the reference numbers 34D' and 34D" and extend under the loop section 34A' on the proximal side of the locking member 36', between that loop section and the locking member. From there the sections 34D' and 34D" extend back through the passageway 108 in the tamping member 106 and through the tensioning assembly in the introducer instrument in the same manner as section 34D.

Placement and operation of the closure 20' is the same as described with reference to closure 20.

As should be appreciated by those skilled in the art, the use of the doubled over filament, with the sections 34B' and 34B" extending from opposite sides of the anchoring member, and with the sections 34C' and 34C" also extending from opposite sides of the anchoring member, balances the load on the anchor member (i.e., it eliminates torque about the longitudinal axis of the anchor member) when tension is applied to the filament sections 34D' and 34D" during the placement procedure.

It should be pointed out at this juncture that a closure constructed in accordance with this invention can be configured to make use of the doubled over filament arrangement of closure 20', but with a three aperture locking member 36, like that of closure 20. In such an alternative construction each leg of the loop section 34A' is extended into a respective aperture 36A and 36B, whereas the doubled extending sections 34D' and 34D" are extended through the third aperture 36C and under the loop section 34A'. Other alternative constructions for the filament, locking member, plug, and anchoring member may be designed as desired. For example, the locking member may have one or more recesses in it, instead of apertures through which portions of the filament extend.

As should be appreciated from the foregoing, the deployment of the closure devices of this invention is easy, quick and reliable and anchoring or locking of the closure in place against accidental displacement is automatic upon tensioning of the filament.

Without further elaboration the foregoing will so fully illustrate our invention that others may, by applying current or future knowledge, adopt the same for use under various conditions of service.

What is claimed is:

1. A closure device for sealing a percutaneous puncture in the wall of a blood vessel, duct, or lumen of a living being, the puncture comprising an opening in the wall of the blood vessel, duct, or lumen, and a tract contiguous with the opening and extending through tissue overlying the vessel, duct, or lumen, said closure device comprising anchoring means, sealing means, filament means, and locking means, said anchoring means being arranged to be brought into engagement with the interior tissue of the vessel, duct, or lumen contiguous with the opening, said sealing means and said locking means being arranged to be located within the tract, said filament means being coupled to said anchoring means, said sealing means, and said locking means, said sealing means being arranged to be moved toward said anchoring means to a puncture sealing position in the tract, said filament means comprising an engagement portion, a first filament portion, and a second filament portion, said engagement portion being coupled to said locking means, said first filament portion extending between said locking means and said anchoring means, said second filament portion being arranged for extending from said anchoring means through the tract, said second filament portion being arranged to be pulled in a proximal direction to cause said engagement portion of said filament means to engage said second filament portion to hold said locking means in position, whereupon said sealing means is held in said puncture sealing position.

2. The closure device of claim 1 wherein said engagement portion of said filament means is adapted to be located adjacent said locking means within the tract.

3. The closure device of claim 1 wherein said sealing means is located between said locking means and said anchoring means.

4. The closure device of claim 1 wherein said engagement portion of said filament means comprises a loop through which a portion of said second filament portion extends.

5. The closure device of claim 4 wherein said loop is arranged to tighten about said portion of said second filament portion when said second filament portion is pulled in the proximal direction.

6. The closure device of claim 5 wherein said loop frictionally engages said portion of said second filament portion when said second filament portion is pulled in the proximal direction.

7. The closure device of claim 4 wherein said locking means comprises a member having at least one opening therein, with said loop extending through said at least one opening to a position located proximally of said member.

8. The closure device of claim 7 wherein said locking means comprises at least a second opening, with said second filament portion extending from said anchoring means through said at least one second opening and through said loop portion.

9. The closure device of claim 4 wherein said filament means comprises an elongated flexible filament, with said loop forming one end of said filament, with said second filament portion forming the other end of said filament, and with said first filament portion forming an intermediate portion of said filament.

10. The closure device of claim 1 whereupon the application of the pulling force on said second filament portion, causes said first filament portion to be placed in tension, said engagement portion of said filament means engaging said second filament portion to maintain said tension in said first filament portion to hold said sealing means in the puncture sealing position and thereby prevent said sealing means from moving away from said anchoring means.

11. The closure of claim 1 wherein said anchoring means has a longitudinal axis and wherein said filament means is coupled to said anchoring means in an arrangement to eliminate torque about said axis of said anchoring means.

12. A closure device for sealing a percutaneous puncture in the wall of a blood vessel, duct, or lumen of a living being, the puncture comprising an opening in the wall of the blood vessel, duct, or lumen, and a tract contiguous with the opening and extending through tissue overlying the vessel, duct, or lumen, said closure device comprising anchoring means, sealing means, filament means, and locking means, said anchoring means being arranged to be brought into engagement with the interior tissue of the vessel, duct, or lumen contiguous with the opening, said locking means being arranged to be located within the tract, said sealing means being arranged to be located within the tract between said locking means and said anchoring means, said filament means comprising an engagement portion, a first filament portion, and a second filament portion, said engagement portion being coupled to said locking means, said first filament portion extending between said locking means and said anchoring means, said second filament portion being arranged for extending from said anchoring means through the tract, said locking means being arranged to be moved toward said anchoring means to a puncture sealing position in the tract, said second filament portion being arranged to be pulled in a proximal direction to cause said engagement portion of said filament means to engage said second filament portion to hold said locking means in said puncture sealing position, whereupon the spacing between said locking means and said filament means becomes fixed and said closure is locked in place in the puncture.

13. The closure device of claim 12 wherein said engagement portion of said filament means comprises a loop through which a portion of said second filament portion extends.

14. The closure device of claim 13 wherein said loop is arranged to tighten about said portion of said second filament portion when said second filament portion is pulled in the proximal direction.

15. The closure device of claim 14 wherein said loop frictionally engages said portion of said second filament portion when said second filament portion is pulled in the proximal direction.

16. The closure device of claim 12 wherein said locking means comprises a member having at least one opening therein, with said loop portion extending through said at least one opening to a position located proximally of said member.

17. The closure device of claim 16 wherein said locking means comprises at least a second opening, with said second filament portion extending from said anchoring means through said at least one second opening and through said loop portion.

18. The closure device of claim 12 wherein said filament means comprises an elongated flexible filament, with said loop portion forming one end of said filament, with said second filament portion forming the other end of said filament, and with said first filament portion forming and intermediate portion of said filament.

19. The closure of claim 12 wherein said anchoring means has a longitudinal axis and wherein said filament means is coupled to said anchoring means in an arrangement to eliminate torque about said axis of said anchoring means.

20. A closure device for sealing a percutaneous puncture in the wall of a blood vessel, duct, or lumen of a living being, the puncture comprising an opening in the wall of the blood vessel, duct, or lumen, and a tract contiguous with the opening and extending through tissue overlying the vessel, duct, or lumen, said closure device comprising anchoring means, sealing means, and filament means, said anchoring means being arranged to be brought into engagement with the interior tissue of the vessel, duct, or lumen contiguous with the opening, said filament means being coupled to said anchoring means and to said sealing means, said sealing means having a proximal portion and a distal portion and being arranged to be moved toward said anchoring means to a puncture sealing position in the tract, said filament means comprising a first looped section and a second extending section, said first looped section being arranged to be located within the tract proximally of said sealing means, said first looped section forming a tightenable passageway, said second extending section being arranged to be located within the puncture tract and extending proximally from said anchoring means along said sealing means and through said tightenable passageway, whereupon a portion of said second extending section is located proximally of said first looped section, said first looped section of said filament means being arranged to be operated to cause said tightenable passageway to frictionally engage said second extending section and thereby form a non-slip joint therebetween to hold said sealing means in said puncture sealing position.

21. The closure device of claim 20 wherein said portion of said second extending section of said filament means located proximally of said first looped section is adapted to be grasped and pulled in the proximal direction, whereupon said first looped section of said filament means is operated to cause said tightenable passageway to frictionally engage said second extending section.

22. The closure device of claim 20 additionally comprising a member having at least one opening therein, with said first looped section of said filament means extending through said at least one opening to a position located proximally of said member, said member and said first looped section of said filament means forming locking means for said closure.

23. The closure device of claim 22 wherein said member has at least one second opening, with said second extending section of said filament means extending from said anchoring means through said at least one second opening and through said first looped section of said filament means.

24. The closure device of claim 20 wherein said filament means is arranged to have a pulling force applied thereto in a proximal direction, whereupon said pulling force causes said second extending section of said filament means to be placed in tension and said first looped section of filament means brought into frictional engagement with said second extending section to maintain said tension therein to hold said sealing means in the puncture sealing position and thereby prevent said sealing means from moving away from said anchoring means.

25. The closure device of claim 24 additionally comprising a member having at least one opening therein, with said first looped section of said filament means extending through said at least one opening to a position located proximally of said member, said member and said first looped section of said filament means forming locking means for said closure.

26. The closure device of claim 25 wherein said member has at least one second opening, with said second extending portion of said filament means extending from said anchoring means through said at least one second opening and through said first looped of said filament means.

* * * * *